United States Patent [19]

Shevade et al.

[11] Patent Number: 5,531,986
[45] Date of Patent: Jul. 2, 1996

[54] LOW RESIDUE ANTIPERSPIRANT SOLID STICK COMPOSITION

[75] Inventors: Makarand Shevade, Plainsboro; Robert J. Bianchini, Belle Mead; Wilson Lee, Bloomfield, all of N.J.

[73] Assignee: The Mennen Company, Morristown, N.J.

[21] Appl. No.: 269,786

[22] Filed: Jul. 1, 1994

[51] Int. Cl.⁶ .............................. A61K 7/38; A61K 7/32
[52] U.S. Cl. .................................. 424/68; 424/65
[58] Field of Search ........................ 424/68, 65

[56] References Cited

U.S. PATENT DOCUMENTS

| | | | |
|---|---|---|---|
| 4,126,679 | 11/1978 | Davy et al. | 424/68 |
| 4,265,878 | 5/1981 | Keil | 424/68 |
| 4,774,079 | 9/1988 | Shin et al. | 424/66 |
| 4,822,602 | 4/1989 | Sabatelli | 424/68 |
| 4,822,603 | 4/1989 | Farris et al. | 424/68 |
| 4,919,934 | 4/1990 | Deckner, et al. | 424/68 |
| 4,944,937 | 7/1990 | McCall | 424/68 |
| 5,008,103 | 4/1991 | Raleigh et al. | 424/66 |
| 5,169,626 | 12/1992 | Tanner et al. | 424/68 |
| 5,194,262 | 3/1993 | Goldberg et al. | 424/47 |
| 5,225,188 | 7/1993 | Abrutyn et al. | 424/68 |
| 5,250,291 | 10/1993 | Park et al. | 424/66 |
| 5,254,332 | 12/1993 | Greczyn et al. | 424/68 |
| 5,302,381 | 4/1994 | Greczyn et al. | 424/68 |

*Primary Examiner*—Shelley A. Dodson
*Attorney, Agent, or Firm*—Antonelli, Terry, Stout & Kraus

[57] ABSTRACT

Disclosed is a low residue antiperspirant solid stick composition containing, in addition to an antiperspirant active material, volatile and non-volatile silicone materials, dimethicone copolyol and high-melting-point and low-melting-point waxes. The composition not only has low visible (white) residue after application and after drying, but also has good cosmetic properties, superior antiperspirancy and is easy to manufacture.

28 Claims, No Drawings

LOW RESIDUE ANTIPERSPIRANT SOLID STICK COMPOSITION

BACKGROUND OF THE INVENTION

The present invention is directed to an antiperspirant solid stick composition. In particular, the present invention is directed to an antiperspirant solid stick composition which is silicone-based and contains silicone materials and waxy-type materials; which leaves little, or substantially no, visible (e.g., white) residue on skin after application and after drying, has superior antiperspirant efficacy and superior cosmetic properties, and is easy to manufacture; and which easily glides on during application and has a powdery feel upon application, and is not sticky or tacky after drying.

Wax-based stick compositions, which contain a wax-type solidifying agent, are known. It is also known to incorporate an antiperspirant active material, such as aluminum-zirconium-glycine complexes, in such wax-based stick compositions, to provide an antiperspirant solid stick. See, e.g., U.S. Pat. No. 4,919,934 to Deckner, et al, the contents of which are incorporated herein by reference in their entirety. However, it is difficult to provide such wax-based antiperspirant solid stick composition which easily glides on during application and which leaves little or no visible residue on the skin after application and after drying.

Various underarm formulations containing alkylmethylsiloxanes are also known. See, e.g., U.S. Pat. No. 5,225,188 to Abrutyn, et al, the contents of which are incorporated herein by reference in their entirety.

There have been attempts to provide low-residue antiperspirant solid sticks. See, for example, U.S. Pat. No. 4,822,603 to Farris, et al; U.S. Pat. No. 5,169,626 to Tanner, et al; U.S. Pat. No. 5,254,332 to Greczyn, et al; and U.S. Pat. No. 5,302,381 to Greczyn, et al, the contents of each of which are incorporated herein by reference in their entirety.

However, it is still desired to provide an antiperspirant solid stick composition with reduced visible (white) residue on the skin after application and after drying, which composition has good cosmetic characteristics and can be easily manufactured.

SUMMARY OF THE INVENTION

It is a first object of the present invention to provide an antiperspirant solid stick composition having low (substantially no) visible (white) residue on the skin after application and after drying, and a method of making and of using such antiperspirant solid stick composition.

It is a further object of the present invention to provide an antiperspirant solid stick composition that does not crumble when being applied, and which has a stable solid matrix.

It is a further object of the present invention to provide an antiperspirant solid stick composition that does not form a sticky or tacky film upon application and has good cosmetic feel (for example, has a powdery feel) on application, and is not sticky and is not tacky after drying.

It is a still further object of the present invention to provide an antiperspirant solid stick composition having good cosmetic attributes, including easy glide-on application.

It is a still further object of the present invention to provide an antiperspirant solid stick composition having superior antiperspirancy and which is easy to manufacture, and methods of making and of using such antiperspirant solid stick composition.

The foregoing objects are achieved by a silicone-based antiperspirant solid stick composition including, in addition to an antiperspirant active material, the following necessary components:

(1) Volatile silicone material (e.g., volatile silicone fluid);
(2) Non-volatile silicone material (e.g., non-volatile silicone fluid);
(3) Dimethicone copolyol;
(4) High-melting-point wax; and
(5) Low-melting-point wax.

The composition according to the present invention desirably includes, in addition to the foregoing necessary components, inert fillers and/or emollients. In addition, other known materials, for example, fragrances, bacteriostats and/or bacteriocides, fillers, colorants, etc., known in the art as components of antiperspirant solid sticks, can also be incorporated in the antiperspirant solid stick composition of the present invention.

Illustratively, compositions according to the present invention include the following components, in amounts as set forth in the following (the following percents being percents by weight, of the total weight of the composition):

(1) 10%–60% (most preferably 30%–40%) volatile silicone material;
(2) 5.01%–50% (most preferably 5.01%–15%) non-volatile silicone material;
(3) 1%–15% dimethicone copolyol;
(4) 2%–10% high-melting-point wax;
(5) 2%–30% low-melting-point wax; and
(6) 10%–30% antiperspirant active material (such as aluminum-zirconium chlorohydrate glycine complex).

Desirably, the composition also includes 1%–15% inert filler (such as cornstarch, talc and/or clay), and 1%–10% emollient (such as PEG-8-distearate), these percentages also being in percent by weight, of the total weight of the composition.

By providing the antiperspirant solid stick composition (e.g., silicone-based antiperspirant solid stick composition) having volatile and non-volatile silicone materials, dimethicone copolyol and high- and low-melting-point waxes, a composition leaving substantially no visible residue when applied to the skin and after drying is achieved. Moreover, such composition has good cosmetic feel on application and good feel after drying, is non-sticky and non-tacky after drying, easily glides on during application, and can be easily manufactured.

DETAILED DESCRIPTION OF THE INVENTION

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present disclosure, where compositions are described as including or comprising specific components, it is contemplated that compositions of the present invention also consist essentially of, or consist of, the recited components. Accordingly, throughout the present disclosure any described composition can consist essentially of, or consist of, the recited components.

The present invention contemplates a low residue, antiperspirant solid stick composition containing, in addition to an antiperspirant active material, both volatile and non-volatile silicone materials, dimethicone copolyol and both low-melting-point and high-melting-point waxes. This composition is, e.g., a silicone-based solid stick composition.

By incorporating the dimethicone copolyol, the volatile silicone material, and the non-volatile silicone material, with the low-melting-point and high-melting-point waxes and antiperspirant active material (e.g., antiperspirant active metal salt), a stick with reduced visible residue after application and after drying is achieved. Moreover, such stick has good cosmetic attributes, including a powdery feel and easy glide-on during application, and a non-sticky or non-tacky film after drying. Moreover, solid stick compositions according to the present invention have a stable matrix (e.g., do not crumble while being applied), have superior antiperspirancy, and are easy to manufacture.

Desirably, the stick composition according to the present invention also includes inert filler materials and emollients, to improve cosmetic attributes. Such emollients illustratively include (but are not limited to) various ethoxylated/propoxylated surfactants, such as PPG-14 butyl ether (e.g., Fluid AP by Union Carbide Corp.), or PEG-8-distearate mentioned previously, or mixtures of emollients. The inert filler can be cornstarch, as mentioned previously, and/or talcum powder (magnesium silicate), fumed silica and/or inorganic clays, polyethylene, or mixtures of these inert particulate materials. Preferably, the inert filler, in particulate form, should have physical properties (e.g., size, shape, etc.) that are similar to those of the antiperspirant active material (e.g., antiperspirant active metal salt).

Specific inert fillers and emollients have been described in the foregoing. However, inert fillers and/or emollients which can be incorporated in the stick compositions of the present invention are not limited to those specifically described in the foregoing, and can be others as known in the art, illustrated in U.S. patents previously referred to herein and incorporated by reference herein.

As mentioned previously, various known components of antiperspirant solid sticks can also be incorporated in the solid stick compositions according to the present invention, such known components including fragrances, bacteriostats, etc. Known bacteriostats include bacteriostatic quaternary ammonium compounds such as 2-amino-2-methyl-1-propanol (AMP), cetyl-trimethylammonium bromide, cetyl pyridinium chloride, 2,4-4'-trichloro-2'-hydroxydiphenylether (Triclosan), etc., and various zinc salts. The bacteriostat can, illustratively, be included in the composition in an amount of 0.2–1.0% by weight, of the total weight of the composition.

Various fragrances known in the art can also be incorporated in the antiperspirant solid stick composition of the present invention. These fragrances can be incorporated in amounts known in the art, e.g., 0.5–3.0% by weight of the total weight of the composition.

The compositions according to the present invention can include additional components that improve glide of the stick composition on the skin. For example, the compositions according to the present invention can include fatty acid esters or amides, or ethoxylated fatty acids, or a combination of such ingredients, to improve glide on the skin. Specific examples include PPG-14-butyl ether (e.g., Fluid AP, by Union Carbide Corp.) and diisopropyl adipate (e.g., Unimate DIPA, from Union Camp Co.). These components can be included in an amount of 1.0–25.0% by weight, of the total weight of the composition. Other materials which can be included to improve glide are polyhydric alcohols, including glycols, and ethoxylated derivatives thereof; these include glycerin, propylene glycol, dipropylene glycol, etc., and illustratively can be included in an amount of 1.0%–20.0% by weight of the total weight of the composition.

Volatile silicone materials known for use in antiperspirant stick compositions, are useful in the present invention. By "volatile" silicone material, we mean a material that has a measurable vapor pressure at ambient temperatures. The volatile silicone material is preferably either a cyclic or a linear polydimethylsiloxane.

The cyclic polydimethylsiloxanes preferably have from about 3 to about 7 silicon atoms, more preferably from about 4 to about 5 silicon atoms. The general formula for such silicone materials is

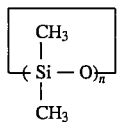

where n=3–7.

The linear polydimethylsiloxanes contain from about 3 to about 9 silicon atoms and have the general formula

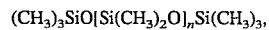

wherein n=1–7.

An illustrative volatile silicone material is cyclomethicone, such as Dow Corning 245 Fluid (DC 245), or Dow Corning 345 Fluid (DC 345). The volatile silicone material is included in the composition in an amount of 10–60%, preferably 30–40%, by weight, of the total weight of the composition.

The non-volatile silicone material, or non-volatile silicone fluid, can be a polyalkylsiloxane, polyalkylarylsiloxane or polyethersiloxane copolymer. An illustrative non-volatile silicone material useful in the present invention is phenyltrimethicone (an illustrative one being Dow Corning 556 Fluid (by Dow Corning Corp.)). Another illustrative non-volatile silicone material useful for the present invention is GE Silicone SF 1150 (by General Electric Silicones). The non-volatile silicone material is included in the composition in an amount of 5.01–50%, preferably 5.01–15%, by weight, of the total weight of the composition.

The composition according to the present invention also includes both high-melting-point and low-melting-point waxes. The low-melting-point waxes have a melting point of from about 37° C. to about 65° C., and the high-melting-point waxes have a melting point of from about 65° C. to about 102° C., preferably 65°–80° C.

Illustrative high-melting-point waxes include beeswax, spermaceti, carnauba, baysberry, candulilla, montan, ozokerite, ceresin, paraffin, castor wax, synthetic waxes such as Fisher-Tropsch waxes, microcrystalline waxes, ethylene glycol diesters, triglyceride (preferably $C_{18}$–$C_{36}$) waxes and ethylene/vinyl acetate copolymers, and mixtures thereof.

Specific castor waxes illustratively include MP-80 and MP-70; as indicated previously, beeswax, carnauba wax, or other natural waxes and petroleum-based waxes may be used in place of (or in addition to) the castor wax. In addition, derivatized waxes, such as hexanediol behenyl beeswax (Koster Keuunen), silicone waxes, such as stearoxytrimethylsilane, an example of which is DC 580 (by Dow Corning), and synthetic waxes, such as Syncrowax HGL-C ($C_{18}$ to $C_{36}$ mixed acid triglycerides, from Croda), with a preferred melting point of 65°–80° C., can be used as the high-melting-point wax. The high-melting-point wax is desirably utilized in an amount of 2%–15% by weight, of the total weight of the composition.

Low-melting-point waxes usable in the present invention include fatty acids, fatty alcohols, fatty acid esters and fatty acid amides, having fatty chains of from about 8 to about 30 carbon atoms, preferably from about 12 to about 18 carbon atoms, and mixtures thereof. Illustrative low-melting-point waxes include cetyl alcohol, palmitic acid, myristyl alcohol, stearyl alcohol, paraffin, cetyl stearate, cetyl palmitate, cetyl myristate, stearyl stearate and mixtures thereof. Also illustrative of the low-melting-point waxes is silicone waxes such as stearoxy dimethicone. A specific low-melting-point wax utilizable according to the present invention is stearyl alcohol (Lanette 18, by Henkel Corp.). The low-melting-point wax is desirably incorporated in the composition in an amount of 2–30% by weight, of the total weight of the composition.

The dimethicone copolyol incorporated in the composition according to the present invention is one or more polymers of dimethylsiloxane with polyoxyalkylene (e.g., polyoxyethylene and/or polyoxypropylene). The dimethicone copolyol incorporated in the composition of the present invention can be a mixture of different dimethicone copolyols. These copolyols are described in U.S. Pat. No. 4,822,602 to Sabatelli, the contents of which are incorporated herein by reference in their entirety, as one or more polyalkylene oxide modified dimethylpolysiloxanes. These copolyols, in terms used in the description in U.S. Pat. No. 4,265,878 to Keil, the contents of which are incorporated herein by reference in their entirety, are polydimethylsiloxanepolyoxyalkylene copolymers containing polydimethylsiloxane segments and polyoxyalkylene segments. As discussed in U.S. Pat. No. 4,265,878, the segments can be either a block arrangement of segments, as illustrated (but not limited) by the formula AB or ABA, where A denotes a polyoxyethylene segment and B denotes a polydimethyl siloxane segment, or a pendant arrangement of segments. Dimethicone copolyols useful according to the present invention are described in the patent literature. Preferred dimethicone copolyols for incorporation in compositions according to the present invention are ABA or AB type block copolymers (polyether block copolymers). The ABA type is illustrated by, but not limited to, compounds of the following structure:

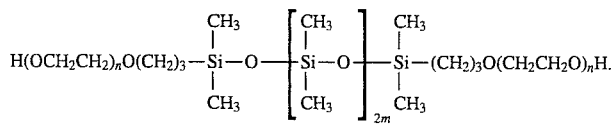

The AB type is illustrated by, but not limited to, compounds of the following structure:

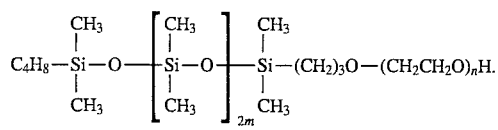

Preferred ABA or AB type dimethicone copolyols are those where n in the foregoing two formulae ranges from 8–32, and which have an HLB (hydrophilic-lipophilic balance) ranging from 3.5 to 8.9. In the foregoing formulae, m and 2m represent a number of repeating dimethylsiloxane units. A most preferred dimethicone copolyol for incorporation in compositions according to the present invention is an ABA type polyether block copolymer, having n=16 in the above formula and having an HLB=5.8.

While the foregoing describes AB or ABA type block dimethicone copolyols as preferred types of dimethicone copolyol for incorporation in compositions of the present invention, the present invention is not limited to use of such types; other types of dimethicone copolyols, e.g., branched types, can also be used.

An illustrative dimethicone copolyol useable according to the present invention is DC 2501 (by Dow Corning Corp.). DC 2501 is a water-dispersible, non-volatile silicone wax that has some water solubility, and that is an ABA polyether block copolymer; that is, DC 2501 is a blocked ABA ethoxylated [EO] methyl siloxane (that is, EO—Si—O—Si—O—Si—EO, the methyl groups not being shown).

The present invention is not limited to use of any specific dimethicone copolyol, and dimethicone copolyols of various molecular weights may be used, in order to impart ease of glide and to improve rigidity of the stick. For example, use of a copolyol with increased molecular weight provides a stick with increased rigidity; with melting point being indicative of molecular weight of the copolyol, a preferred melting point of the copolyol is 35°–60° C.

The dimethicone copolyol is preferably incorporated in the stick composition in an amount of 1%–15% by weight, of the total weight of the composition.

Preferably, a minimum combined (total) amount of silicones (volatile and non-volatile silicone materials, and dimethicone copolyol) in the composition is 40% by weight, of the total weight of the composition.

The antiperspirant active material can be any conventional antiperspirant material, including (but not limited to) antiperspirant active metal salts. These antiperspirant active metal salts include, but are not limited to, aluminum-zirconium tri-, tetra- and penta-chlorohydrate glycine complexes, which are coordination complexes of aluminum-zirconium tri-, tetra- or penta-chlorohydrate and glycine in which some of the water molecules normally coordinated to the metal have been displaced by the glycine. An illustrative antiperspirant active metal salt includes aluminum-zirconium tetrachlorohydrex gly (for example, Reach AZP-908 and Reach 908-0, each manufactured by Reheis Corp.), which are coordination complexes of aluminum-zirconium tetrachlorohydrate and glycine in which some of the water molecules normally coordinated to the metal have been displaced by the glycine. The present invention is not limited to use of aluminum-zirconium tetrachlorohydrex gly, and other antiperspirant active metal salts (such as aluminum chlorohydrate), and/or other antiperspirant active materials, can be utilized in the stick composition of the present invention. Illustratively, antiperspirant solid stick compositions according to the present invention contain the antiperspirant active material in an amount of 10–30% by weight, of the total weight of the composition. Moreover, the preferred antiperspirant material particulate (e.g., antiperspirant metal salt particulate) has a median particle size of less than 100 microns, a bulk density of 20–40 pounds/cubic foot and a spherical particle shape. Most preferred is a median particulate size of 20–40 microns.

The antiperspirant sticks of the present invention may be manufactured using methods known in the art. Typically, the ingredients are combined and heated to melt the components (other than the inert filler), and the melted components (together with particulate inert filler) are mixed. Desirably, volatile materials, such as the fragrance material, are incorporated in the composition in the latter stages of the mixing cycle, in order to avoid volatilization thereof. After mixing, the molten composition can be poured into stick-form molds (e.g., dispensing containers), as conventional in the art, after which the compositions harden into a solid.

The compositions according to the present invention can be utilized by the consumer, to reduce perspiration, as conventional antiperspirant solid stick compositions are used. An end of the molded composition can be elevated out of the dispensing container, so as to protrude out of the dispensing container, and rubbed against the skin in the axillary region, for example, so as to deposit antiperspirant active material in the axillary region, which prevents (or at least reduces) perspiration from the axillary region. Thus, by rubbing the composition of the present invention against the skin in regions of the body particularly prone to perspiration (for example, the axillary region), perspiration wetness in such regions can be controlled.

In the following are set forth examples of the present invention. These examples are illustrative, and not limiting, of the present invention. In the following examples, all amounts are in percent by weight, of the total weight of the composition.

The following Example 1 is illustrative of the present invention, and shows that the composition of the present invention leaves reduced visible residue on the skin as applied and particularly after drying, as compared to a commercially available antiperspirant stick (Comparative Example 1).

|  | Example 1 | Comparative Example 1 |
| --- | --- | --- |
| Cyclomethicone DC 345 | 31.0 | 41.0% |
| Stearyl Alcohol Lanette 18M | 20.0% | 12.0% |
| Phenyltrimethicone DC 556 | 10.0% | — |
| Dimethicone Copolyol DC 2501 | 7.0% | — |
| Castor wax MP-80 (Caschem Co.) MP-70 | 4.0% | 8.0% |
| PEG-8-Distearate | 4.0% | — |
| Glyceryl Stearate PEG 100 | — | 1.0% |
| PPG-14 Butyl Ether | — | 6.5% |
| Antiperspirant Active Material |  |  |
| Reach 908-O | 20.0% |  |
| Reach AZP-908 |  | 22.0% |
| Cornstarch | 3.0% | — |
| Talc |  | 8.5% |
| Fragrance | QS | QS |

The procedure for forming the composition of Example 1 is as follows: To a vessel equipped with heating and stirring apparatus the silicone fluids DC 345 (cyclomethicone) and DC 556 (phenyltrimethicone) are added. The temperature is brought to 75° C., and the stearyl alcohol is added with mixing until completely dissolved. Next, PEG-8-Distearate and the castor wax are added with mixing, while maintaining the temperature at 75°–80° C. DC 2501 (dimethicone copolyol) is added with mixing, and the mixture is stirred until complete dissolution is achieved. The antiperspirant active material, in particulate form, and cornstarch are added portion-wise in sequence, allowing approximately 10 minutes of mixing between each addition. The batch temperature is gradually lowered to 60° C., and the fragrance is added with mixing. The batch is stirred for an additional 30 minutes, and then cooled to 52°–54° C. While still in the liquid state, the product is poured into the appropriate mold, cooled in a refrigerator for 30 minutes, and allowed to set for an additional 30 minutes at room temperature. The solid stick is ready for use.

Example 1 and Comparative Example 1 were tested as to visible residue left after application and after drying, by subjective evaluation by a panel of ten people (male and female). Compositions of both Example 1 and Comparative Example 1 were applied on the skin with four even strokes, the panelists being asked to visually rate the products on a 1–5 scale (where 1 is no residue present and 5 is extensive residue present). Initial ratings and ratings after thirty minutes were assessed. The data is given in the following Table I.

TABLE I

|  | INITIAL |  | FINAL (30 min) |  |
| --- | --- | --- | --- | --- |
| Panelist | Example I | Comp. Ex. 1 | Example I | Comp. Ex. 1 |
| 1. | 1 | 4 | 1 | 3 |
| 2. | 1 | 2 | 1 | 2 |
| 3. | 1 | 4 | 1 | 2 |
| 4. | 1 | 3 | 1 | 2 |
| 5. | 1 | 3 | 1 | 2 |
| 6. | 1 | 5 | 1 | 3 |
| 7. | 1 | 4 | 1 | 3 |
| 8. | 1 | 5 | 1 | 3 |
| 9. | 1 | 4 | 1 | 3 |
| 10. | 1 | 4 | 1 | 4 |

As can be seen in Table I, the composition of Example I has a lower residue as compared to that of Comparative Example 1.

Example 2

| Component | Wt. % |
| --- | --- |
| Cyclomethicone DC 345 | 30.0% |
| Stearyl Alcohol Lanette 18 | 20.0% |
| Phenyltrimethcone DC 556 | 10.0% |
| Dimethicone Copolyol DC 2501 | 7.0% |
| Syncrowax HGL-C | 4.0% |
| PEG-8-Distearate | 4.0% |
| Antiperspirant Active Material Reach 908-0 | 20.0% |
| Cornstarch | 3.0% |
| Fragrance | QS |

This composition is similar to the composition of Example 1, but replaces the castor wax with a synthetic wax (Syncrowax HGL-C). The product is formulated as in Example 1. The product has good feel and improved application properties.

Example 3

| Component | Wt. % |
| --- | --- |
| Cyclomethicone DC 345 | 30.0% |
| Stearyl Alcohol Lanette 18 | 20.0% |
| Phenyltrimethicone DC 556 | 5.0% |
| Dimethicone Copolyol DC 2501 | 7.0% |
| Castor Was MP-80 | 4.0% |
| PEG-8-Distearate | 4.0% |
| Unimate DIPA | 5.0% |
| Antiperspirant Active Material Reach 908-O | 20.0% |
| Cornstarch | 4.0% |
| Fragrance | QS |

This composition includes a fatty acid ester (Unimate DIPA) to improve glide. The product is formulated as in Example 1. The Unimate DIPA is added after the dimethicone copolyol. The product has good feel, improved application and cosmetic properties.

Example 4

| Component | Wt. % |
| --- | --- |
| Cyclomethicone DC 345 | 30.0% |
| Stearyl Alcohol Lanette 18 | 20.0% |
| Phenyltrimethicone DC 556 | 10.0% |
| Dimethicone Copolyol DC 2501 | 7.0% |
| Castor Wax MP-80 | 4.0% |
| PEG-8-Distearate | 4.0% |
| Antiperspirant Active Material Reach 908-O | 20.0% |
| Talc-Luzennac Supra A | 4.0% |
| Fragrance | QS |

This composition includes talc as an inert filler, rather than cornstarch as in Example 1. The product is formulated as in Example 1. The product has good feel and improved powdery, talcum-like application properties. Talcum is more economical than cornstarch.

Example 5

| Component | Wt. % |
| --- | --- |
| Cyclomethicone DC 345 | 31.0% |
| Stearyl Alcohol Lanette 18 | 19.0% |
| Phenyltrimethicone DC 556 | 10.0% |
| Dimethicone Copolyol DC 2501 | 7.0% |
| Beeswax (hexane-diol behenyl) | 4.0% |
| PEG-8-Distearate | 4.0% |
| Antiperspirant Active Material Reach 908-O | 20.0% |
| Talc-Luzennac Supra A | 4.0% |
| Fragrance | QS |

This composition uses beeswax as the high-melting-point wax, rather than castor wax used in Example 1. The product is formulated as in Example 1. The product has good feel and improved application rigidity.

Accordingly, by the present invention an antiperspirant solid stick composition having reduced visible (white) residue on the skin after application and after drying, yet also having easy glide-on application, a solid stable matrix, superior antiperspirancy, excellent cosmetic attributes, and a powdery feel on application, in a stick composition which is not sticky or tacky after drying, is achieved. Moreover, such composition is easy to manufacture.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A low-residue, silicone-based antiperspirant solid stick composition comprising:
   (a) a volatile silicone material;
   (b) a non-volatile silicone material;
   (c) a high-melting-point wax;
   (d) a low-melting-point wax;
   (e) dimethicone copolyol; and
   (f) an antiperspirant active material, wherein a total of volatile silicone material, non-volatile silicone material and dimethicone copolyol included in the composition is at least 40% by weight of the total weight of the composition, the composition comprising, in percent by weight of the total weight of the composition, 10%–60% volatile silicone material, 5.01%–50% non-volatile silicone material, 2%–10% high-melting-point wax, 2%–30% low-melting-point wax, 1%–15% dimethicone copolyol, and 10%–30% antiperspirant active material.

2. The low-residue, silicone-based antiperspirant solid stick composition according to claim 1, wherein the composition further includes an inert filler and an emollient.

3. The low-residue, silicone-based antiperspirant solid stick composition according to claim 2, comprising, in percent by weight of the total weight of the composition, 1%–15% inert filler and 1%–10% emollient.

4. The low-residue, silicone-based antiperspirant solid stick composition according to claim 3, wherein the volatile silicone material is cyclomethicone, the non-volatile silicone material is phenyltrimethicone, the high-melting-point wax is castor wax, the low-melting-point wax is stearyl alcohol, the antiperspirant active material includes an antiperspirant active metal salt, the inert filler is selected from the group consisting of cornstarch, talc and clay, and the emollient is PEG-8-distearate.

5. The low-residue, silicone-based antiperspirant solid stick composition according to claim 2, wherein the volatile silicone material is cyclomethicone, the non-volatile silicone material is phenyltrimethicone, the high-melting-point wax is castor wax, the low-melting-point wax is stearyl alcohol, the antiperspirant active material includes an antiperspirant active metal salt, the inert filler is selected from the group consisting of cornstarch, talc and clay, and the emollient is PEG-8-distearate.

6. The low-residue, silicone-based antiperspirant solid stick composition according to claim 1, wherein the volatile silicone material is cyclomethicone, the non-volatile silicone material is phenyltrimethicone, the high-melting-point wax is castor wax, the low-melting-point wax is stearyl alcohol, and the antiperspirant active material includes an antiperspirant active metal salt.

7. The low residue, silicone-based antiperspirant solid stick composition according to claim 3, wherein the high-melting-point wax is a synthetic wax.

8. The low-residue, silicone-based antiperspirant solid stick composition according to claim 7, wherein the synthetic wax is a $C_{18}$ to $C_{36}$ acid triglyceride.

9. The low residue, silicone-based antiperspirant solid stick composition according to claim 8, wherein the volatile silicone material is cyclomethicone, the non-volatile silicone material is phenyltrimethicone, the low-melting-point wax is stearyl alcohol, the antiperspirant active material includes an antiperspirant active metal salt, the inert filler is selected from the group consisting of cornstarch, talc and clay, and the emollient is PEG-8-distearate.

10. The low residue, silicone-based antiperspirant solid stick composition according to claim 1, wherein the high-melting-point wax is a synthetic wax.

11. The low residue, silicone-based antiperspirant solid stick composition according to claim 10, wherein the synthetic wax is a $C_{18}$ to $C_{36}$ acid triglyceride.

12. The low residue, silicone-based antiperspirant solid stick composition according to claim 11, wherein the volatile silicone material is cyclomethicone, the non-volatile silicone material is phenyltrimethicone, the low-melting-point wax is stearyl alcohol, and the antiperspirant active material includes an antiperspirant active metal salt.

13. The low residue, silicone-based antiperspirant solid stick composition according to claim 3, wherein the dimethicone copolyol is an AB or ABA dimethicone copolyol, B denoting a polydimethylsiloxane segment and A denoting a polyoxyethylene segment.

14. The low residue, silicone-based antiperspirant solid stick composition according to claim 1, wherein the dimethicone copolyol is an AB or ABA dimethicone copolyol, B denoting a polydimethysiloxane segment and A denoting a polyoxyethylene segment.

15. A method for controlling perspiration wetness, comprising applying the antiperspirant solid stick composition of claim 3 to axillary regions of a human.

16. A method for controlling perspiration wetness, comprising applying the antiperspirant solid stick composition of claim 2 to axillary regions of a human.

17. A method for controlling perspiration wetness, comprising applying the antiperspirant solid stick composition of claim 1 to axillary regions of a human.

18. A method of reducing visible residue resulting from application of an antiperspirant solid stick, comprising incorporating dimethicone copolyol, non-volatile silicone material and volatile silicone material, in an antiperspirant solid stick composition also containing both high-melting-point and low-melting-point waxes and an antiperspirant active material, so as to form a silicone-based antiperspirant solid stick composition, a total amount of dimethicone copolyol, non-volatile silicone material and volatile silicone material incorporated in the silicone-based antiperspirant solid stick composition being at least 40% by weight, of the total weight of the silicone-based antiperspirant solid stick composition, wherein the silicone-based antiperspirant solid stick composition comprises, in percent by weight of the total weight of the silicone-based antiperspirant solid stick composition, 10%–60% volatile silicone material, 5.01%–50% non-volatile silicone material, 2%–10% high-melting-point wax, 2%–30% low-melting-point wax, 1%–15% dimethicone copolyol, and 10%–30% antiperspirant active material.

19. The method according to claim 18, wherein the antiperspirant solid stick composition further includes an inert filler and an emollient.

20. The method according to claim 18, wherein the high-melting-point wax is a synthetic wax.

21. The method according to claim 20, wherein the synthetic wax is a $C_{18}$ to $C_{36}$ acid triglyceride.

22. The low-residue, silicone-based antiperspirant solid stick composition according to claim 1, wherein the composition includes, in percent by weight of the total weight of the composition, 30%–40% volatile silicone material and 5.01%–15% non-volatile silicone material.

23. The method according to claim 18, wherein the composition includes, in percent by weight of the total weight of the silicone-based antiperspirant solid stick composition, 30%–40% volatile silicone material and 5.01%–15% non-volatile silicone material.

24. The low-residue, silicone-based antiperspirant solid stick composition according to claim 1, wherein the composition further includes at least one additional component that improves glide of the stick composition on the skin, selected from the group consisting of fatty acid esters, fatty acid amides, ethoxylated fatty acids and polyhydric alcohols.

25. The low-residue, silicone-based antiperspirant solid stick composition according to claim 24, wherein said at least one additional component is selected from the group consisting of PPG-14-butyl ether, diisopropyl adipate, glycerin, propylene glycol and dipropylene glycol.

26. The low-residue, silicone-based antiperspirant solid stick composition according to claim 1, wherein the non-volatile silicone material is selected from the group consisting of polyalkylsiloxane, polyalkylarylsiloxane, and polyethersiloxane copolymers.

27. The low-residue, silicone-based antiperspirant solid stick composition according to claim 26, wherein the dimethicone copolyol is an AB or ABA dimethicone copolyol, B denoting a polydimethylsiloxane segment and A denoting a polyoxyethylene segment, the copolyol having 8–32 oxyethylene groups and having an HLB ranging from 3.5 to 8.9.

28. The low-residue, silicone-based antiperspirant solid stick composition according to claim 1, consisting essentially of the volatile silicone material, the non-volatile silicone material, the high-melting-point wax, the low-melting-point wax, the dimethicone copolyol and the antiperspirant active material.

* * * * *